United States Patent [19]

Jones

[11] 4,175,953
[45] Nov. 27, 1979

[54] NON-PRECIOUS DENTAL ALLOY OF CO-NI-CR CONTAINING SI AND B

[75] Inventor: Robin F. Jones, Titusville, N.J.

[73] Assignee: Johnson & Johnson, New Brunswick, N.J.

[21] Appl. No.: 920,430

[22] Filed: Jun. 29, 1978

[51] Int. Cl.$^2$ .................. C22C 30/00; C22C 19/05
[52] U.S. Cl. .................. 75/134 F; 75/171; 433/207
[58] Field of Search .......... 75/134 F, 171; 32/2, 32/10 A

[56] References Cited

U.S. PATENT DOCUMENTS

| | | | |
|---|---|---|---|
| 2,155,047 | 4/1939 | Grossman | 75/171 |
| 2,936,229 | 5/1960 | Shepard | 75/0.5 |
| 3,437,480 | 4/1969 | Cape | 75/170 |
| 3,914,867 | 10/1975 | Manning et al. | 32/2 |
| 4,038,074 | 7/1977 | Davitz | 75/171 |
| 4,038,752 | 8/1977 | Phelps et al. | 32/2 |
| 4,108,642 | 8/1978 | Chiaramonte | 75/134 F |

OTHER PUBLICATIONS

T. Sims et al., "Superalloys", Wiley, N.Y., 1972, pp. 577 and 579 (FIG. 1).

*Primary Examiner*—L. Dewayne Rutledge
*Assistant Examiner*—Upendra Roy

[57] ABSTRACT

A dental alloy is described which is comprised of from 13 to 25% Cr, 20 to 40% Ni, 3 to 7.5% Mo, 0.2 to 1.0% B, 2.75 to 5.0% Si, less than 5% Mn and from 30 to 60 Co. This alloy is especially useful as a substitute for the precious metal alloys used to fabricate dental prosthetic appliances.

9 Claims, No Drawings

NON-PRECIOUS DENTAL ALLOY OF CO-NI-CR CONTAINING SI AND B

FIELD OF THE INVENTION

A non-precious metal alloy useful in the fabrication of dental prosthetic appliances. This alloy comprises from 13 to 25% Cr, 20 to 40% Ni, 3 to 7.5% Mo., 0.2 to 1.2% B, 2.75 to 5.0% Si, less than 5% Mn and from 30 to 60% Co. The instant alloy shows improved castability, strength, hardness and ductility. Furthermore, unlike some of the prior art non-precious metal alloys, it can be melted with a natural gas-oxygen torch.

BACKGROUND OF THE PRIOR ART

Non-precious metal alloys have been known as substitutes for the gold alloys used in fabricating dental prosthetic appliances for many years. However, despite the fact that gold is much more expensive than these alloys, dental technicians appear to prefer the gold alloys. Gold is found to exhibit many desirable physical characteristics including low melting point, ductibility, ability to form impact resistant porcelain to metal bonds, ease of polishability and solderability, etc. Therefore, in order for the economic advantage of the non-precious metal alloys to be considered by the dental technician most of the desirable physical characteristics of gold must be matched.

U.S. Pat. Nos. 2,156,757; 2,162,252; 2,165,793; and 2,165,849 teach the use of non-precious metal alloys in place of gold for dentals. These alloys include Ni, Co and Cr, to which boron is added to reduce the propensity of Cr to form a high melt slag. It is noted by the patentee that boron increases castability and fluidity of the alloys. However, the alloys taught in these patents all contain at least 1 and preferably 5% boron to achieve improved castability and fluidity. Such amounts of boron as taught by the patentee would be detrimental in that ductility and ease of polishability would be poorer. This may explain why the alloys taught in these patents (which were invented prior to 1939) have not achieved commercial success as dental alloys.

At about the same time other patentees were teaching the addition of zirconium to nickel-chromium alloys to improve their use as a dental alloy (see U.S. Pat. No. 2,180,288) and adjusting the amounts of carbon and Mo in cobalt chromium alloys for the same purpose. (See U.S. Pat. No. 2,246,288). Neither of these patents suggest means to improve the castability of the rather high melting alloys disclosed therein.

Other patentees have added various other elements in minor amounts to the well known Co, Ni and Cr alloys to make them suitable for dental applications. See for example, U.S. Pat. No. 3,756,809 and 3,837,838 wherein tantalum and niobium are added to form intermetallics with cobalt and thereby strengthening the alloy. Again, there is no teaching as to providing good castability to these rather high melting alloys.

In U.S. Pat. No. 2,309,136 a Ni-Cu alloy is added to a Co, Cr, and Mo alloy to form a product useful in dental applications. The patentee states that it is critical to his invention to have copper in this alloy to insure that the alloy does not phase separate. The instant novel alloys specifically exclude copper which is known to cause hot shortness in alloy casting and to cause discoloration during the firing of porcelain on gold restoration.

U.S. Pat. No. 3,865,585 teaches a dental alloy having a critical concentration of nitrogen to achieve the patentee's goal of having improved ductility without the loss of tensile strength in a dental alloy. The instant novel alloy does not require nitrogen although some nitrogen may be incorporated during the melting process used to prepare the alloy.

The patentees, of U.S. Pat. Nos. 3,907,555 and 3,841,868 add gallium and tin or tin alone, respectively to a Ni, Cr, and Mo dental alloy to improve castability. The instant novel alloys show improved castability without the use of gallium or tin. Moreover, tin and gallium are low melting elements and would probably be difficult to control during the initial formulation of the alloy.

U.S. Pat. No. 3,716,418 teaches the use of an 80-20 Ni-Cr alloy as a dental alloy. The teaching of this patent is limited to adding very slight amounts of Fe and Mn to the basic alloy to form a special oxide surface which improves bonding of the alloy to porcelain. This modification is outside the scope of the instant invention.

In U.S. Pat. No. 3,749,507 the patentee adds Mo, Be, and Al to the 80-20 alloy mentioned above. Be and Al are necessary ingredients of this alloy; Al improving the strength and Be increasing the fluidity. However, neither of these elements are desirable in the alloys of the instant invention in that Al tends to decrease the castability of remelted alloys and Be is extremely hazardous to health in its oxide form.

In U.S. Pat. No. 3,464,817 the patentee found that maintaining the cobalt level below 22% and the aluminum level below 6% resulted in dental alloy having polishability without the loss of necessary physical characteristics such as yield strength, etc. As in the previously mentioned patent, the alloy disclosed in this reference excludes Al and Be neither of which are desirable in the instant novel alloys.

In U.S. Pat. No. 3,544,315, the patentee finds that maintaining the Mo and C in critical amounts advantageously limits the hardness of a Ni, Co, and Cr alloy while maintaining its strength. The critical amounts defined therein are not necesssary in the instant alloys. Furthermore, although the patentee suggests incorporating silicon in his alloy, the silicon is taught to function as a deoxidizer and therefore must be below 1%. The patentee states that the boron content must be maintained below 0.01%. Both of these limitations are unnecessary and/or undesirable in the instant alloys.

U.S. Pat. No. 3,914,867 teaches a dental alloy which includes niobium, tin and Al as well as the Ni, Cr, Mo, Si and B combination claimed herein. The patentee points out that all of the ingredients disclosed are critical for his purpose of providing a dental alloy having the properties of low melting temperature and outstanding physical properties. There is no suggestion that excluding Nb, Sn and Al would result in the desirable physical properties (from the standpoint of dental use) of the novel alloy disclosed herein.

Other references which teach alloys which are similar to those disclosed herein include: U.S. Pat. Nos. 3,922,168; 3,713,175; 3,658,515; 2,868,667; 970,364; 2,875,043; 2,714,760; 3,930,848; 3,925,072; 4,012,227; 3,900,316 and 3,892,541. These alloys are not suggested for use as dental alloys and therefore because of the very stringent requirements for such dental alloys it is believed that this art is not relevant in that the same objects are not being sought in these references.

SUMMARY OF THE INVENTION

The present invention comprises a non-noble metal alloy and the prosthetic dental appliances produced therefrom, which metal alloy is designed to be a substitute for gold alloys in the fabrication of prosthetic dental appliances employing porcelain to metal bonds, which alloy is based on the combination of nickel, cobalt and chromium with a lesser inclusion of other elements necessary to impart the desired properties to be described herein, including an acceptable level of tensile strength, the capacity of forming durable impact resistant bond with dental porcelain, low melting point so that casting is facilitated, ductility so that the dentist may make minor adjustment without fear of damaging the prosthetic dental appliance, polishability, hardness comparable to natural teeth so that the patient's natural teeth are not damaged by contacting said alloy, a coefficient of expansion slightly greater than dental porcelain so that the porcelain of the prosthetic dental appliance is in a state of compression after firing, solderability, but excluding or minimizing elements which would tend to discolor porcelain, e.g. copper, iron, etc. or would be dangerous for the manufacturer of said alloy to work with, e.g. beryllium.

DETAILED DESCRIPTION OF THE INVENTION

The alloy compositions of the present invention have the following range of constituents by weight percentages;

|  | Broad | Narrow |
|---|---|---|
| Cobalt | 30–60 | 35–45 |
| Nickel | 20–40 | 30–36 |
| Chromium | 13–25 | 18–21 |
| Molybdenum | 3–7.5 | 4–6 |
| Silicon | 2.75–5.0 | 3–4 |
| Boron | 0.2–1.0 | 0.25–0.75 |
| Manganese | 0–5 | 0–2 |
| Iron | 0–5 | 0–3 |
| Aluminum | 0–0.15 | 0–0.10 |

The above alloys may contain very small amounts of carbon, phosphorous and sulfur as impurities. In general, the total amount of such impurities will not exceed 0.5% by weight, and preferably, on an individual basis, no more than 0.05% sulfur, 0.05% phosphorous, and 0.15% carbon.

The preferred compositions exhibiting most advantageously the properties heretofore described are selected from the foregoing alloys containing essentially no iron, manganese, or aluminum who melting points lie in the range of from about 2,100° F. to about 2,400° F. In this range, the alloys can be melted with a natural gas oxygen torch.

More specifically, the most preferred alloy compositions are obtained from the following group of alloys containing by weight percent:

| cobalt | 35–38 |
|---|---|
| nickel | 33–35 |
| chromium | 18–21 |
| molybdenum | 4.5–5.5 |
| silicon | about 3.5 |
| boron | about 0.5 |

The foregoing compositions, (especially the most preferred alloys) will have all of the above noted desired properties.

For example, by excluding or minimizing the presence of copper, the discoloration of porcelain is minimized. Of course, in the most preferred alloys no porcelain discolorations occur during the firing of the porcelain.

It should be noted, that those skilled in the art have expected that cobalt would cause discoloration of porcelain occur during the firing of porcelain. In the instant alloys, it has unexpectedly been found that up to 60 weight percent cobalt does not discolor the porcelain.

As noted above, the alloys of this invention have a melting point within the range of 2100° to 2400° F. This melting range is ideal in that it is within the range in which the dental laboratories are usually accustomed to work so that the alloy may be cast for the preparation of metal cores and other structural materials without change in equipment and technique. However, the melting temperature of the alloys are ideally suited for dental construction to be faced with a tooth-simulating porcelain covering.

The ultimate tensile strength of the instant alloys ranges from about 80,000 to 125,000 p.s.i., and compares favorably with that of about 80,000 p.s.i. to 90,000 p.s.i. for white gold and 65,000 to 70,000 p.s.i. for yellow gold. The hardness of below about 93.4 on the Rockwell B scale compares favorably with the 91.5 Rockwell B hardness for white gold. Thus, the alloys have strength superior to gold while not being so hard as to prevent grinding and polishing of dental structures to the desired shape and smoothness.

The good corrosion resistance exhibited by the alloys of the present invention may be seen by the minor extent of etching as measured by weight loss after immersion at room temperature, for up to 56 days in lactic acid or Ringer's solution.

In addition to the foregoing, the alloy can be remelted and cast without loss of their excellent physical properties, it may be used with the dental solders presently employed when working with gold or with non-precious metal alloy solders, and may be faced with dental plastic materials such as the acrylics.

The instant alloys are characterized as having excellent castability. For the purposes of non-precious metal dental alloys good castability means that the castability is similar to that of gold. For example, the alloy should melt at a temperature of less than 2400° F. so that the dental technician may use a natural gas-oxygen torch, the molten alloy should be fluid and the point at which the alloy becomes fluid enough to pour into the mold should be easily visualized, and the cast alloy should completely fill the mold and accurately reproduce all the features thereof. The instant alloys by this criteria may be characterized as having good castability.

The instant alloys achieve the above desirable properties by careful selection of the aforementioned metals and controlling the weight percent thereof in the alloy. It should be noted that although some of the metals are known to impart or improve certain of the above desirable properties, in known alloys, it is the specific combination and amounts which achieve all of the desired properties of the instant alloys.

The instant alloys include the nickel-cobalt-chromium base alloy which is known for its strength and corrosion properties. As previously noted, however, those skilled in the art, believed that cobalt would tend to discolor porcelain, and therefore it was believed to be desirable to exclude cobalt from dental alloys.

As previously indicated, the silicon is preferably present in the range of about 2.75 to 5.0% by weight. Where used in amounts much below 2.75, e.g. 2.5%, the fusion temperature of the alloy was sufficiently high to prevent the alloy from being melted by a gas-oxygen torch. When the silicon content is increased too much above 5.0%, it is expected that the alloy will become brittle and lose some of its ductility. For the purposes intended, therefore, it is critical and essential that the silicon content of the alloy be maintained between 2.75 and 5.0% by weight. To maintain the balance of melting point and ductility properties, it is more preferred that the silicon content of the alloy be between 3 and 4 weight percent.

The addition of molybdenum to the nickel, cobalt, chromium and silicon stabilizes the thermal expansion property of the alloy against change which tends to occur during the repeated firing which is a necessary procedure when porcelain is fused to the structural metal during the preparation of jackets, crowns, bridges and the like. Further, molybdenum has the property of further improving corrosion resistance. At molybdenum levels about 7.5%, it is expected that ductility will decrease while at levels below 3.0% the tensile strength decreases to less than that of yellow gold. Therefore, it is more preferable to maintain the molybdenum level at from 4 to 6 weight percent.

It is believed that the inclusion of the boron or manganese improves the bonding strength between the alloy and porcelain. Manganese tends to counteract the detrimental effects of sulfur, however, addition of maganese tends to decrease corrosion resistance and tends to discolor the porcelain. Hence, the preferred alloy compositions contemplate the use of boron. However, it is critical and essential that boron not be employed in excess of about 1.0 by weight since boron tends to increase brittleness and decreases the polishability of the alloy. The preferred range of from 0.25 to 0.75% by weight boron, provides the best balance of bonding strength without increasing brittleness or decreasing polishability.

The dental alloy composition intended for use as structural metal may contain minor amounts of other materials which may be present as impurities in the metals employed to prepare the alloy, such as for example, carbon, sulfur, phosphorous, aluminum. None of these are essential in the dental alloy compositions of the present invention and in general, diminish the desired properties of the alloy. Accordingly, the alloy compositions of the present invention consist essentially of nickel, cobalt, chromium, molybdenum, silicon and boron or less preferably, manganese.

The alloy may be prepared in a conventional manner such as by placing the components in a fused alumina crucible and fusing the ingredients with appropriate mixing. While in the molten state, the alloy may be poured into molds for ingot formation.

The dental alloys of the present invention intended for use as structural metals may be employed in the replacement of the denser and more expensive gold which has been the conventional structural metal used for dental purposes. The alloys are ideally suited for use where bonding of the alloy to a porcelain is required, as in the preparation of artificial teeth, crowns, bridges and the like.

The following samples (except for white gold) were prepared by melting together the essentially pure metals in the amounts listed and heating until the melt was homogeneous. As is well known in the art, the actual amounts of the metals in the samples may vary somewhat but not enough to alter the results obtained in a significant manner.

The specific melting procedure employed comprised melting nickel, cobalt and molybdenum in an air induction furnace at a temperature of 2850° F. The silicon and boron was added to this melt and the temperature dropped to about 2500° F. and the entire melt aspiration cast into Vycor rods. The rods were cut into lengths of $\frac{1}{4}"$ to 1", melted in a small induction furnace and cast into investments having the desired configuration for testing. The testing methods have been described in U.S. Ser. No. 546,642 filed on Feb. 3, 1975 in the name of Pei Sung and Irving Klaus is hereby incorporated by reference for the purpose of describing the method of bonding porcelain to the instant novel alloys. It is contemplated that the invention includes the method of bonding porcelain to dental castings of the instant novel alloys to fabricate prosthetic dental appliances as well as such appliances.

The following are specific embodiments of the instant invention. There is no intent, however, to be limited to such embodiments since many modifications within the spirit of the invention will be obvious to one skilled in the art with this disclosure before him.

Example I
Chromium Effects

| Alloy | Co | Cr | Ni | Mo | Si | B | Mn | UTS (psi) | YS (psi) | % Elong. | Modulus of Elasticity (psi) | Coeff. of Therm. Exp. $\times 10^{-6}$ in/°C. | Castability (microns) | Melting Point °F. | Porcelain Bonding % Retention | Hardness As Cast | Hardness After 5 Firings |
|---|---|---|---|---|---|---|---|---|---|---|---|---|---|---|---|---|---|
| A | Bal. | 20 | 34 | 5.0 | 3.5 | 0.5 | 0.5 | 109,700 | 68,600 | 5.03 | $25.39 \times 10^6$ | 14.22 | 70.4 | 2220 | 90.0 | 94.0 $R_B$ | 95.3 $R_B$ |
| B | Bal. | 18 | 4 | 5.0 | 3.5 | 0.5 | 0.7 | 108,300 | 62,300 | 5.37 | $26.57 \times 10^6$ | 13.40 | 84.1 | — | — | 92.3 $R_B$ | 92.0 $R_B$ |
| C | Bal. | 22 | 3 | 5.0 | 3.5 | 0.5 | 0.7 | 126,700 | 73,100 | 4.54 | $26.07 \times 10^6$ | 14.26 | 85.1 | — | 67.9 | 92.3 $R_B$ | 96.9 $R_B$ |
| D | Bal. | 24 | 3 | 5.0 | 3.5 | 0.5 | 0.7 | 110,500 | 66,300 | 4.51 | $27.41 \times 10^6$ | 13.69 | 53.9 | — | 66.0 | 93.9 $R_B$ | 95.0 $R_B$ |
| WHITE GOLD | | | | | | | | 88,000 | 61,000 | 10 | — | 13.75 | 130 | 2350 | — | 91.5 B | — |

MECHANICAL PROPERTIES

This example demonstrates that the level of chromium is very important in the instant novel alloys in that ductility decreases as chromium increases.

Example II
Manganese Effects

| Alloy | Co | Cr | Ni | Mo | Si | B | Mn | UTS (psi) | YS (psi) | % Elong. | Modulus of Elasticity (psi) | Coeff. of Therm. Exp. $\times 10^{-6}$ in/°C. | Castability (microns) | Melting Point °F. | Porcelain Bonding % Retention | Hardness As Cast | Hardness After 5 Firings |
|---|---|---|---|---|---|---|---|---|---|---|---|---|---|---|---|---|---|
| A | Bal. | 20 | 34 | 5.0 | 3.5 | 0.5 | 0.5 | 109,700 | 68,600 | 5.03 | $25.39 \times 10^6$ | 14.22 | 70.4 | 2220 | 90.0 | 94.0 $R_B$ | 95.3 $R_B$ |
| E | Bal. | 20 | 34 | 5.0 | 3.5 | 0.5 | — | 106,600 | 65,600 | 4.16 | $26.07 \times 10^6$ | — | 91.1 | — | 71.1 | 82.4 $R_B$ | 97.0 $R_B$ |
| F | Bal. | 20 | 34 | 5.0 | 3.5 | 0.5 | 1.5 | 102,900 | 62,600 | 5.22 | $21.21 \times 10^6$ | — | 105.0 | — | 81.8 | 91.8 $R_B$ | 96.8 $R_B$ |

MECHANICAL PROPERTIES

It should be noted that Manganese may detrimentally effect corrosion and cause discoloration of porcelain. However, it is believed that (especially in combination with boron) manganese will improve the bonding of the alloy to the porcelain.

Example III
Nickel Effects

| Alloy | Co | Cr | Ni | Mo | Si | B | Mn | MECHANICAL PROPERTIES ||||| Coeff. of Therm. Exp. $\times 10^{-6}$ in/°C. | Castability (microns) | Melting Point °F. | PORCELAIN BONDING % Retention | HARDNESS As Cast | HARDNESS After 5 Firings |
|---|---|---|---|---|---|---|---|---|---|---|---|---|---|---|---|---|---|
| | | | | | | | | UTS (psi) | YS (psi) | % Elong. | Modulus of Elasticity (psi) | | | | | | |
| A | Bal. | 20 | 34 | 5.0 | 3.5 | 0.5 | 0.5 | 109,700 | 68,600 | 5.03 | 25.39 $\times 10^6$ | 14.22 | 70.4 | 2220 | 90.0 | 94.0 $R_B$ | 95.3 $R_B$ |
| G | Bal. | 20 | 30 | 5.0 | 3.5 | 0.5 | 0.7 | 110,000 | 75,300 | 3.32 | 29.26 $\times 10^6$ | — | 74.9 | — | 72.5 | 95.0 $R_B$ | 90.6 $R_B$ |
| H | Bal. | 20 | 38 | 5.0 | 3.5 | 0.5 | 0.7 | 100,600 | 67,100 | 4.60 | 23.55 $\times 10^6$ | — | 85.6 | — | 71.1 | 91.6 $R_B$ | 97.0 $R_B$ |

It should be noted that in contrast to chromium, increasing nickel content increases the ductility of the alloy.

Example IV
Molybdenum Effects

| Alloy | Co | Cr | Ni | Mo | Si | B | Mn | MECHANICAL PROPERTIES ||||| Coeff. of Therm. Exp. $\times 10^{-6}$ in/°C. | Castability (microns) | Melting Point °F. | PORCELAIN BONDING % Retention | HARDNESS As Cast | HARDNESS After 5 Firings |
|---|---|---|---|---|---|---|---|---|---|---|---|---|---|---|---|---|---|
| | | | | | | | | UTS (psi) | YS (psi) | % Elong. | Modulus of Elasticity (psi) | | | | | | |
| I | Bal. | 20 | 34 | 0 | 3.5 | 0.5 | 0.7 | 95,400 | 52,900 | 5.08 | 26.55 $\times 10^6$ | 14.77 | 52.3 | — | 88.0 | 95.7 $R_B$ | 72.4 $R_B$ |
| J | Bal. | 20 | 34 | 2.5 | 3.5 | 0.5 | 0.7 | 110,000 | 61,900 | 7.30 | 28.9 $\times 10^6$ | 14.35 | 53.1 | — | 70.7 | 96.7 $R_B$ | 83.4 $R_B$ |
| A | Bal. | 20 | 34 | 5.0 | 3.5 | 0.5 | 0.5 | 109,700 | 68,600 | 5.03 | 25.39 $\times 10^6$ | 14.22 | 70.4 | 2220 | 90.0 | 94.0 $R_B$ | 95.3 $R_B$ |
| K | Bal. | 20 | 34 | 7.5 | 3.5 | 0.5 | 0.5 | 104,500 | 62,000 | 4.85 | 26.32 $\times 10^6$ | 13.68 | 116 | 2192 | 83.1 | 92.0 $R_B$ | 94.7 $R_B$ |

It should be noted that molybdenum is necessary to provide a yield strength at least equal to white gold. However, above the upper limits claimed herein ductility and castability is inadequate for a dental alloy.

Example V
Silicon Effects

| Alloy | Co | Cr | Ni | Mo | Si | B | Mn | MECHANICAL PROPERTIES ||||| Coeff. of Therm. Exp. ×10⁻⁶ in./°C. | Castability (microns) | Melting Point °F. | PORCELAIN BONDING % Retention | HARDNESS |||
|---|---|---|---|---|---|---|---|---|---|---|---|---|---|---|---|---|---|
| | | | | | | | | UTS (psi) | YS (psi) | % Elong. | Modulus of Elasticity (psi) | | | | | As Cast | After 5 Firings |
| A | Bal. | 20 | 34 | 5.0 | 3.5 | 0.5 | 0.5 | 109,700 | 68,600 | 5.03 | 25.39 ×10⁶ | 14.22 | 70.4 | 2220 | 90.0 | 94.0 R$_B$ | 95.3 R$_B$ |
| L | Bal. | 20 | 34 | 5.0 | 2.5 | 0.5 | 0.7 | 113,000 | 69,700 | (...could not be cast...) | 24.3 ×10⁶ | 14.11 | 53.9 | — | — | — | — |
| M | Bal. | 20 | 34 | 5.0 | 5.0 | 0.5 | 0.7 | | | 4.25 | | | | — | 60.0 | 92.1 R$_B$ | 95.0 R$_B$ |

It should be noted that at the lower level shown for silicon, the sample could not be melted with the air-gas torch used by the dental technician. However, at the upper limit shown, ductility is becoming inadequate.

Example VI
Boron Effects

| Alloy | Co | Cr | Ni | Mo | Si | B | Mn | MECHANICAL PROPERTIES ||||| Coeff. of Therm. Exp. ×10⁻⁶ in./°C. | Castability (microns) | Melting Point °F. | POCELAIN BONDING % Retention | HARDNESS |||
|---|---|---|---|---|---|---|---|---|---|---|---|---|---|---|---|---|---|
| | | | | | | | | UTS (psi) | YS (psi) | % Elong. | Modulus of Elasticity (psi) | | | | | As Cast | After 5 Firings |
| A | Bal. | 20 | 34 | 5.0 | 3.5 | 0.5 | 0.5 | 109,700 | 68,600 | 5.03 | 25.39 ×10⁶ | 14.22 | 70.4 | 2220 | 90.0 | 94.0 R$_B$ | 95.3 R$_B$ |
| N | Bal. | 20 | 34 | 5.0 | 3.5 | 0.25 | 0.7 | 81,300 | 60,600 | 3.16 | 27.1 ×10⁶ | 13.94 | 69.7 | — | 82.0 | 81.9 R$_B$ | 83.6 R$_B$ |
| O | Bal. | 20 | 34 | 5.0 | 3.5 | 1.0 | 0.7 | 123,700 | 73,100 | 2.76 | 28.42 ×10⁶ | 13.82 | 27.0 | 2282 | 60.4 | 25 R$_C$ | 33.7 R$_C$ |

It should be noted that increasing the boron content increases hardness and makes the alloy more difficult to polish.

What is claimed is:

1. A dental alloy of good polishability and useful in the fabrication of dental prosthetic devices such as crowns and bridges which have a porcelain covering bonded thereto consisting essentially of from 13 to 25 percent Cr, 20 to 40 percent Ni, 3 to 7.5 percent Mo, 0.2 to 1 percent B, 2.75 to 5 percent Si, less than 5 percent Mn and from 30 to 60 percent Co, by weight.

2. The alloy of claim 1, further characterized as containing essentially from 0 to 5 percent Fe, 0 to 5 percent Mn, 0 to 0.15 percent Al, by weight, and excluding or minimizing the presence of Cu, and having a melting point in the range of from about 2100° F. to about 2400° F.

3. The alloy of claim 2 further characterized as having an ultimate tensile strength of from about 80,000 to 125,000 psi and a Rockwell B hardness of below about 93.4.

4. A dental alloy according to claim 1 consisting essentially of 35 to 45% Co, 30 to 36% Ni, 18 to 21% Cr, 4 to 6% Mo, 3 to 4% Si, 0.25 to 0.75% B, 0 to 2% Mn, 0 to 3% Fe and 0 to 0.10% Al.

5. A dental alloy according to claim 4 consisting essentially of from 35 to 38% Co, 33 to 35% Ni, 18 to 21% Cr, 4.5 to 5.5 Mo about 3.5% Si and about 0.5% B, by weight.

6. A dental restorative construction comprising a metal core of a non-precious metal alloy contoured in a esired form and a porcelain covering bonded thereto, said metal core being of the alloy of claim 1.

7. A dental restorative construction according to claim 6 wherein the procelain is under compression.

8. A dental restorative construction according to claim 6 wherein the metal core is bonded to the porcelain covering with the aid of a bonding agent.

9. A method of preparing a dental construction which comprises:
  (a) preparing a metal core by casting dental alloy of claim 1,
  (b) apply to the surfaces of said metal core a porcelain having coefficients of expansion in the range of from about $10 \times 10^{-6}$ in/in/° C. to about $21 \times 10^{-6}$, and
  (c) firing the pocelain onto said metal core.

* * * * *